(12) United States Patent
Lee et al.

(10) Patent No.: US 7,171,260 B2
(45) Date of Patent: Jan. 30, 2007

(54) ECTOPIC BEAT DETECTION ALGORITHM FOR IMPLANTABLE CARDIAC RHYTHM MANAGEMENT DEVICE

(75) Inventors: Kent Lee, Fridley, MN (US); Apurv Kamath, Solana Beach, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 465 days.

(21) Appl. No.: 10/806,954

(22) Filed: Mar. 23, 2004

(65) Prior Publication Data

US 2005/0216068 A1    Sep. 29, 2005

(51) Int. Cl.
*A61B 5/0468* (2006.01)

(52) U.S. Cl. .............. 600/516; 600/515; 600/518; 607/25

(58) Field of Classification Search ........ 600/508, 600/509, 515, 516, 518; 607/1, 2, 4, 5, 9, 607/14, 17, 25
See application file for complete search history.

(56) References Cited

U.S. PATENT DOCUMENTS

| | | | | |
|---|---|---|---|---|
| 5,417,714 A | * | 5/1995 | Levine et al. ............ | 607/9 |
| 5,549,647 A | * | 8/1996 | Stoop et al. ............. | 607/9 |
| 5,873,895 A | * | 2/1999 | Sholder et al. .......... | 607/9 |
| 6,122,546 A | * | 9/2000 | Sholder et al. .......... | 607/9 |
| 6,487,443 B2 | * | 11/2002 | Olson et al. ............. | 600/518 |
| 6,567,691 B1 | * | 5/2003 | Stadler .................... | 600/515 |
| 6,671,548 B1 | * | 12/2003 | Mouchawar et al. ..... | 600/518 |

* cited by examiner

*Primary Examiner*—Robert E. Pezzuto
*Assistant Examiner*—Eugene Wu
(74) *Attorney, Agent, or Firm*—Nikolai & Mersereau, P.A.; Thomas J. Nikolai

(57) ABSTRACT

A method implemented in a dual chamber cardiac rhythm management device for identifying non-sinus ventricular depolarizations following an atrial event. The PR interval for a sensed ventricular beat that occurs after either an atrial pace or an atrial sensed event is examined and if it falls into a non-physiologic range, it is classified as an ectopic beat. If the PR interval is close to a physiologic range, the RR to AA ratio and a PR interval for the current beat are compared to those for an immediately preceding beat. Attention is also paid to the morphology of the ventricular depolarization in determining whether a beat is ectopic or not.

6 Claims, 3 Drawing Sheets

ECTOPIC BEAT DETECTION ALGORITHM FOR IMPLANTABLE CARDIAC RHYTHM MANAGEMENT DEVICE

BACKGROUND OF THE INVENTION

I. Field of the Invention

This invention relates generally to implantable cardiac rhythm management devices, and more particularly to a method of operating such devices to more correctly classify ventricular beats occurring after an atrial depolarization (either paced or sensed) as an ectopic beat, i.e., a beat of non-sinus origin.

II. Discussion of the Prior Art

A drawback of many present-day automatic implantable defibrillators and cardiac pacemakers is that they normally only identify as a premature ventricular contraction (PVC) a beat that is not preceded by a sensed atrial depolarization. Yet, it has been shown that frequently such ectopic beats do occur following an atrial event. When the implantable device fails to detect ectopic beats, inappropriate indicators can be recorded on the device's stored electrogram. When the electrogram is then read out by a physician, the improperly marked recording strip can lead to errors in diagnosis and/or treatment.

Ectopic ventricular beats that occur after an atrial sense/pace event may be examples of late coupled PVCs, which some authors have discussed as common onset patterns for arrhythmias. Thus, the ability to better detect late-coupled PVCs is important for beat trending and arrhythmia prediction purposes.

The inability to detect all PVCs may also lead to life threatening pacemaker mediated tachycardia (PMT). It is found that in some patients multiple episodes of PMT due to retrograde conduction of an ectopic ventricular beat resulting in the pacer tracking at its maximum tracking rate. To address PMT, state-of-the-art pacemakers and pacemaker/defibrillators employ what is called "post ventricular atrial refractory periods" (PVARP) following a PVC to prevent PVCs from starting a PMT episode. The length of the PVARP tends to be fixed. However, ectopic beats may occur after an atrial sense event, such that the implantable cardiac rhythm management device classifies such beats as a normal ventricular sensed event instead of a PVC. Since there is only a short atrial blanking after a ventricular sense event, these ventricular ectopic beats may have retrograde conduction, causing an erroneous premature atrial sensed event that leads to a PMT episode. The use of a fixed size PVARP after a PVC with post atrial sense PVCs results in undersensing at high rates. By providing a dynamic-sized (rather than fixed) PVARP following an ectopic beat, it can blank the atrial channels after the ectopic beat, retrograde conducted ectopic sensed beats will be prevented from causing PMT, yet at the same time will allow sufficient atrial blanking without atrial undersensing.

In addition, proper identification of non-sinus ventricular beats is critical for heart-rate variability (HRV) measurements, since HRV measurements require intervals that are sinus in origin. HRV, or actually the lack thereof, is a factor in assessing the severability of congestive heart failure. For a discussion of HRV as an indicator of CHF, see "Depressed Heart Rate Variability as an Independent Predicator of Death in Congestive Heart Failure Secondary to Ischemic or Idiopathic Dilated Cardiomyopathy" by Piotr Ponikowski, et al., The American Journal of Cardiology, Vol. 79, Jun. 15, 1997, pp. 1645–1650. Thus, a need exists for a method that can more reliably discriminate between sinus and non-sinus ectopic ventricular sensed beats.

SUMMARY OF THE INVENTION

The present invention provides an improved method for detection of ectopic beats by an implantable cardiac rhythm management device of the type having an atrial event detector, a ventricular event detector and a microprocessor-based controller coupled to the atrial event detector and the ventricular event detector, the microprocessor being programmed to determine PR intervals, RR intervals and AA intervals from detected atrial and ventricular events. The algorithm employed also calls for determining an average time interval between an atrial event and the next occurring ventricular event over a predetermined number of heartbeat cycles. An ectopic beat is then indicated when a PR interval of a given heartbeat cycle is less than about 80 percent of the average PR interval and is also less than about 80 ms in length. Detector accuracy may be increased still further by determining whether the given heartbeat cycle is physiologic when the PR interval of the given heartbeat cycle is less than about 80 percent of the average PR interval over a plurality of cycles and the PR interval of the given heartbeat cycle is greater than about 80 ms. Beats are considered ectopic if the current atrial beats are not PACs, and if the RR/AA ratio is less than 90% of the previous beat, or if the ratio between the current PR interval and the preceding PR interval is less than 60%. Additionally, if the beat polarity is tri-phasic or more, regardless of the timing relationship between RR/AA or PR intervals, then it is considered an ectopic beat.

In assessing whether a given heartbeat cycle is physiologic, the microprocessor-based controller is programmed to compute whether a ratio of a RR interval for the given heartbeat cycle to the AA interval of that cycle is greater than about 90 percent of the that same ratio for an immediately preceding heartbeat cycle and then computing whether the ratio of the length of the PR interval of the given heartbeat cycle to the length of the PR interval for an immediately preceding heartbeat cycle is greater than about 60 percent. If those two conditions are met and the QRS complex of the given heartbeat cycle is biphasic, the algorithm concludes that the beat is physiologic and not an ectopic beat.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
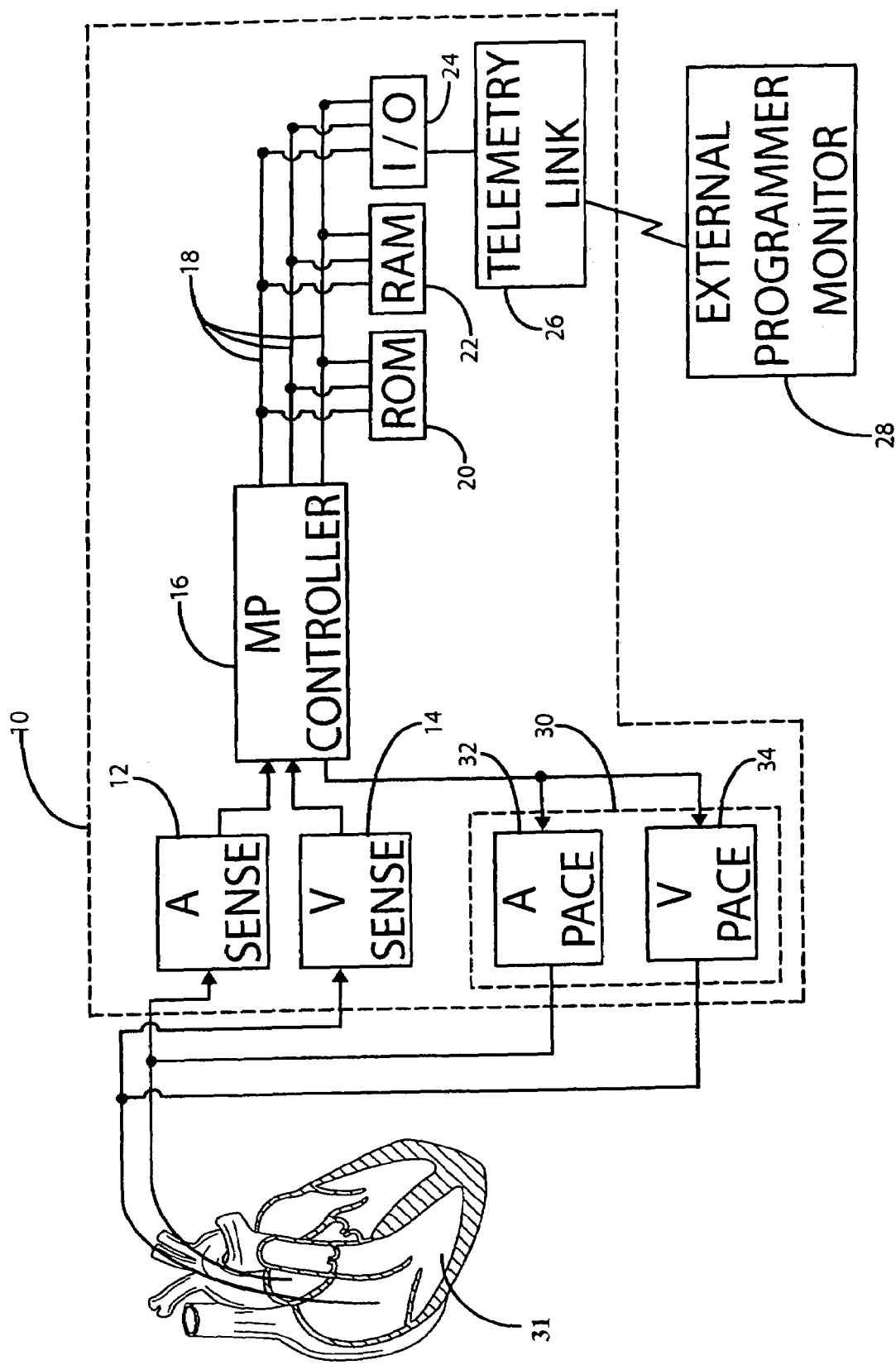
FIG. 1 is a schematic block diagram of an implantable cardiac rhythm management device serving as a platform in which the method of the present invention is carried out.

Referring to FIG. 1, there is shown a logical block diagram of a conventional implantable cardiac rhythm management device which is shown as being enclosed by broken line box 10. The device 10 is adapted to be connected to a patient's heart by means of one or more medical leads. The device is depicted as a dual chamber pacemaker having a first sense amplifier 12 for detecting atrial depolarization signals (P-waves) and a ventricular sense amplifier 14 for detecting ventricular depolarization signals (R-waves). The output signals from the sense amplifiers 12 and 14 are applied as inputs to a microprocessor-based controller 16 which typically includes circuitry for converting analog outputs from the sense amplifiers 12 and 14 to digital values, all as is well known in the art.

The microprocessor-based controller includes a bus 18 for coupling it to a ROM memory 20 that typically stores a program of instructions executable by the microprocessor component in the microprocessor-based controller 16. The bus also provides for bi-directional information flow with respect to a RAM memory 22. Typically, the RAM memory 22 will programmable operating parameters used during the execution of the program stored in the ROM memory 20.

The microprocessor-based controller bus also connects to an input/output circuit 24 that interfaces with a telemetry link 26 whereby data can be exchanged between the implanted device 10 located within the patient and an external programmer/monitor 28 located externally and used by attending medical professional to reprogram various operating parameters and to monitor results computed by the microprocessor-based controller all as is well known in the art.

Without limitation, the microprocessor-based controller 16 is able to compute the length of the interval between successful atrial depolarization (AA interval), the length of the interval between successful ventricular depolarizations (the RR interval), the length of the interval between an atrial depolarization and the next successful ventricular depolarization (PR interval) as well as a running average of PR intervals over a predetermined number of heartbeat cycles ($PR_{AVG}$).

The microprocessor-based controller is connected in controlling relation to a pulse generator, shown enclosed by broken line box 30, for delivering pacing pulses selectively to the atrial chamber of the heart 31 and to its ventricular chamber by the A pace circuit 32 and the V pace circuit 34, respectively, at times determined by the microprocessor-based controller 16.

Figure 2:
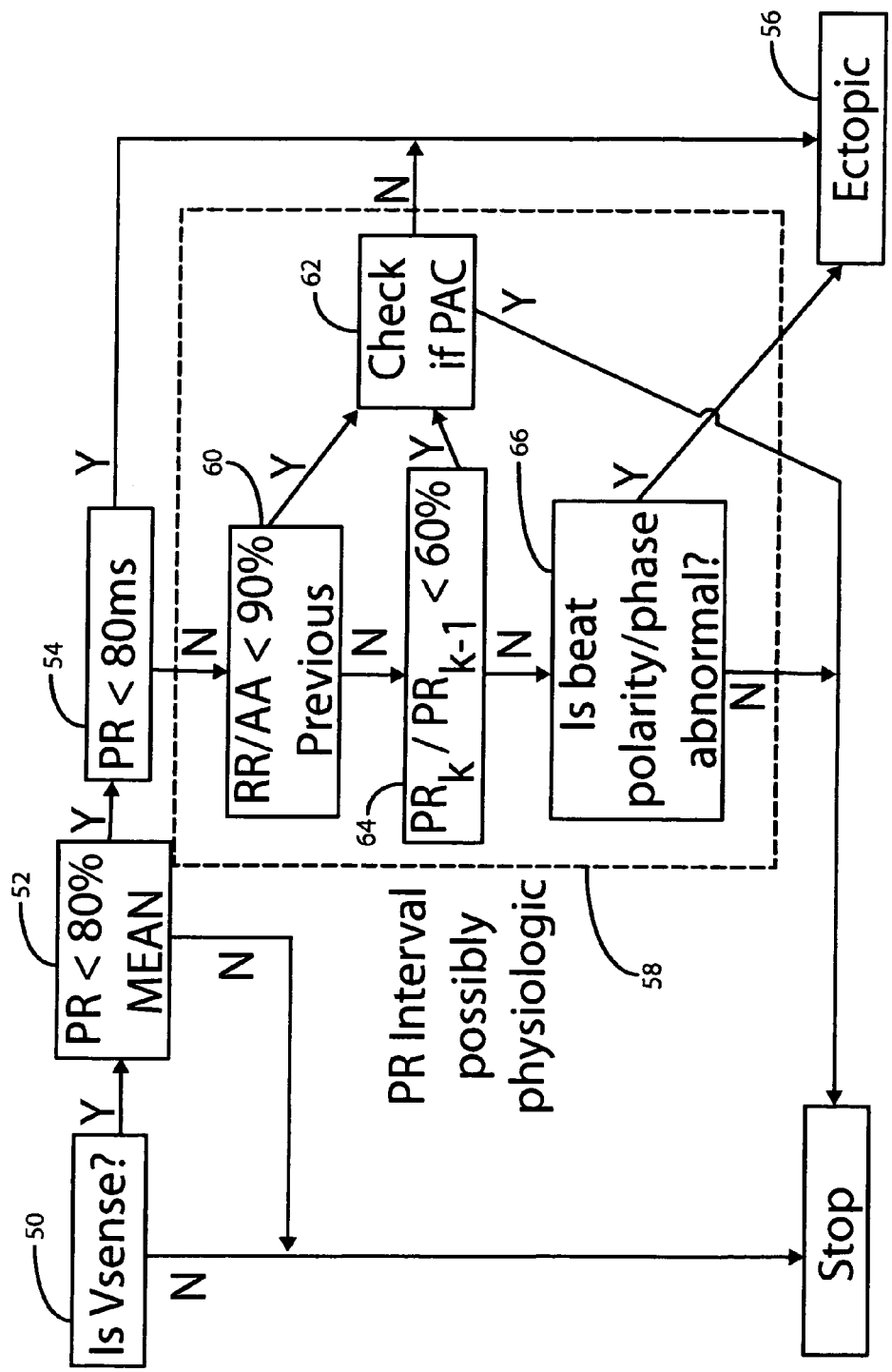
FIG. 2 is a flow chart of the algorithm executed by the microprocessor-based controller for determining whether a sensed ventricular beat following an atrial beat is ectopic.

Turning next to FIG. 2, there is displayed a flowchart of the algorithm comprising the software executed by the microprocessor-based controller 16 that is employed to detect ectopic beats. Initially, a running average of the PR interval length over a predetermined number of beats ($PR_{AVG}$) is computed and stored in the RAM 22. A test is then made at decision block 50 to determine whether a non-paced ventricular beat following the occurrence of an atrial beat is occurring. If so, the length of the PR interval for that beat is determined and a test is made at decision block 52 to determine whether the length of that PR interval is less than a predetermined percent of the earlier determined average PR interval. Without limitation, a factor of about 80% has been found suitable. If not, the beat is not ectopic and the routine stops until a next ventricular beat is sensed. If, however, the PR interval for the beat under consideration is less than the aforesaid percentage of the $PR_{AVG}$, then a further test is made at decision block 54 to see whether the PR interval for the beat under consideration is less than a predetermined length, e.g., which would be indicative of a non-physiologic range. Again, without limitation, the test may be whether PR is less than about 80 ms. If it is less than 80 ms, then an ectopic beat is identified. See block 56.

On the other hand, if the PR interval of the beat under consideration is less than about 80 percent of $PR_{AVG}$, but its PR>80 ms, that beat may possibly be physiologic and the further tests depicted by the decision blocks within the dashed line box 58 are carried out. Specifically, as indicated by decision block 60, the ratio of the RR interval to the AA interval of the beat under consideration is computed and a determination is made whether the computed value is less than about 90 percent of that same ratio for the immediately preceding beat. The ratio of RR to AA is a measurement of ventricular prematurity. That ratio is indicative of rapid changes in PR interval. If RR/AA<90%, a determination is made at block 62 whether the current atrial timing is from a premature atrial contraction (PAC). A PAC is identified as at least two atrial beats without a corresponding ventricular depolarization. If a PAC has not occurred, the beat is identified at being ectopic. On the other hand, if the beat under consideration involves a PAC, the beat cannot be identified as ectopic or physiologic, so no decision is made.

Had the test at decision block 60 indicated that the RR/AA interval was greater than 90 percent of that same ratio for the preceding beat, a test at decision block 64 determines whether the PR interval for the beat under consideration ($PR_k$) is less than about 60 percent of the PR interval for the preceding beat ($PR_{k-1}$). If it is, the test at decision block 62 is again repeated to determine whether a PAC is involved.

Figure 3:
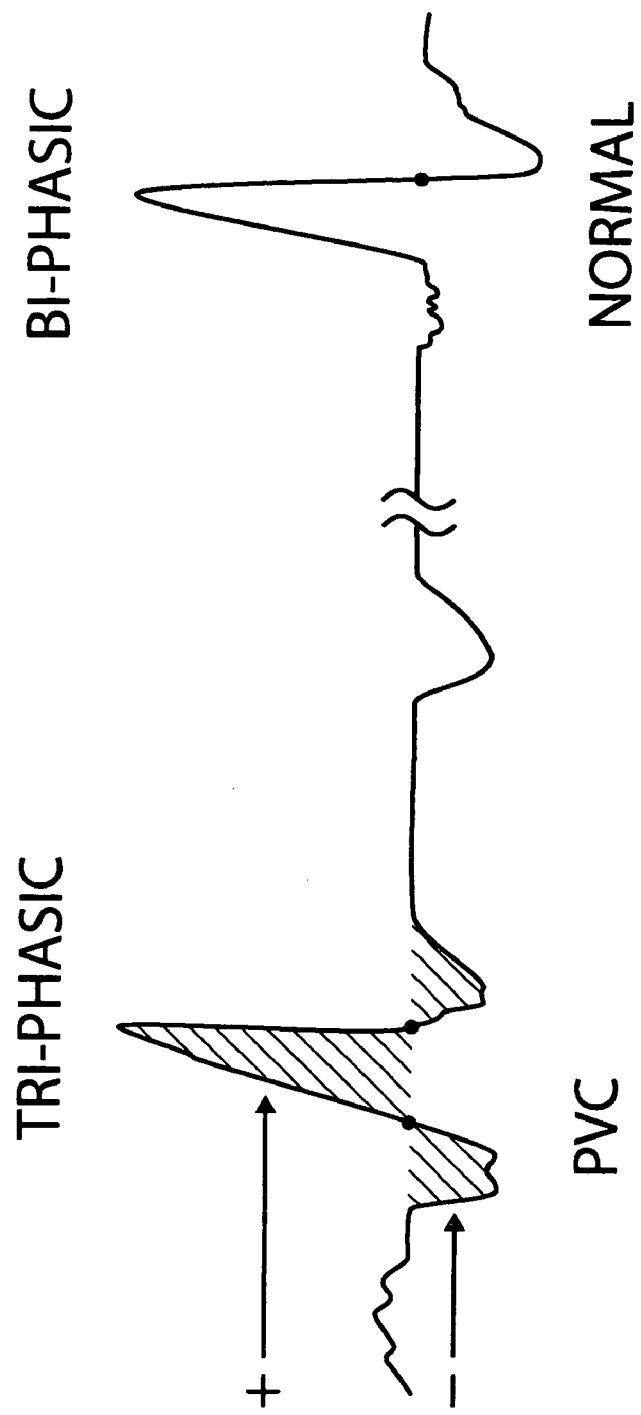
FIG. 3 is a waveform comparing an ectopic beat to a normal beat.

If neither the test at decision block 60 nor at decision block 64 is true, then the morphology of the present beat is examined to determine whether the beat under consideration is either bi-phasic or has more than 2 phases to the beat. See block 66. In order to carry out the test at decision block 66, at each beat detection, a window is formed around the QRS complex and threshold crossings of the beat are examined. The number of phases is determined by the number of threshold crossings within the window. FIG. 3 illustrates a comparison between an ectopic beat and a normal beat. An ectopic or PVC exhibits two zero-crossings while a normal beat has only a single zero-crossing. Thus, if the test at block 66 reveals a triphasic waveform, the beat is identified as ectopic whereas if the waveform is biphasic, a normal beat is involved.

Summarizing the algorithm reflected by the flow chart of FIG. 2, the cardiac rhythm management device can readily measure and store AA, RR, PR and RP intervals. The PR interval for a sensed ventricular beat that occurs after either an atrial paced or an atrial sensed event is examined and if it falls into a nonphysiologic range, e.g., 0 to 80 ms, it is classified as an ectopic beat. If the PR interval is close to a physiologic range, e.g., 80 to 150 ms, other factors are examined to determine whether the beat is ectopic. Specifically, the RR to AA ratio and the PR interval for the current beat is contrasted with that for the immediately preceding beat. Finally, the signal polarity around the beat detection time is monitored to determine whether the beat is biphasic or triphasic in its morphology. If it is determined that a premature atrial contraction is involved, the algorithm cannot determine if the beat is of a sinus or non-sinus nature, so no decision is made.

It can be seen, then, that the method depicted by the flow chart of FIG. 2 describes an algorithm that can be used to correctly classify ventricular depolarizations that occur following an atrial event (sensed or paced) that are actually non-sinus in origin as ectopic beats.

In that the present invention is capable of more accurately detecting ectopic beats, it can be used to prevent or at least reduce episodes of PMT which can occur in dual-chamber pacemakers that are capable of atrial tracking modes, most commonly DDD or VDD. Only patients who are capable of retrograde ventriculoatrial conduction through the AV node or an AV accessory pathway are capable of sustaining this rhythm. The mechanism is identical to any macro reentrant tachycardia seen in the heart in which two electrical pathways exist between the atria and ventricles. PMT is classically initiated by a PVC. The depolarization is then conducted in a retrograde manner to the atria. If the PVARP has ended and the retrograde complex is of sufficient amplitude to be sensed, the atrial channel of the pacemaker senses the event and initiates an AV interval. At the end of the AV interval, the pacemaker then delivers a stimulus to the ventricle and the loop is reinitiated. Although PVCs are the classic cause of pacemaker mediated tachycardia initiation, any situation that results in AV disassociation allowing a ventricular depolarization to occur without a normally coupled atrial-paced or atrial-sensed event, may begin the loop. If the programmed AV interval is long, it may be possible for the AV node to recover in time to conduct the subsequent ventricular-paced event in a retrograde direction, thus initiating another endless loop tachycardia. The absence of antigrade AV nodal conduction does not rule out retrograde conduction over the AV node or concealed AV accessory pathway.

The rate of PMT depends on the conduction velocity and refractory period of the retrograde AV pathway. If the retrograde AV conduction is the same as or shorter than the upper rate interval (but not shorter than the PVARP), the tachycardia rate is at the programmed upper rate limit. If the retrograde AV conduction time is slower than the upper rate interval, the tachycardia rate is below the upper programmed rate. Thus, although the rate of the PMT can never exceed the programmed upper rate of the pacemaker, it may be lower.

The main defense against PMT is the use of an appropriate PVARP interval. During the PVARP, the atrial channel cannot sense the retrograde depolarization that would, in a different set of circumstances, initiate the PMT. This is independent of the source of that atrial event. If retrograde conduction is present during implementation or follow-up, it is a simple matter to measure the ventriculoatrial time and program PVARP to an interval that is longer. Many patients, however, exhibit only intermittent ventriculoatrial conduction, making an accurate assessment difficult. A major limitation of using a long PVARP is that it limits the upper tracking rate of the device. For example, some patients may have ventriculoatrial times in excess of 430 msec. Thus, using a PVARP of 450 msec and an AV interval of 150 msec, the total atrial refractory period is 600 ms. This causes 2:1 blocking at an atrial rate of 100 bpm, which is far too low for an active patient, but which may be appropriate for a sedentary patient.

In the past, the solution to this problem is the use of PMT prevention algorithms, the most common of which is PVARP extension upon detection of a PVC where the PVC is defined as a ventricular-sensed event that is not preceded by an atrial-paced or an atrial-sensed event. When such a PVC is detected, devices in accordance with the prior art prolong PVARP by a fixed or programmable value for the following cycle. This allows a shorter baseline PVARP to be used, with associated higher 2:1 blocking rates.

The prior art method for preventing PMT following the occurrence of a PVC is not complete, since an ectopic beat may occur after a normal atrial sensed-paced event, possibly with retrograde conduction causing PMT without appropriate atrial blanking. To address this problem, the algorithm of the present invention is used to detect PVCs that occur after sensed atrial events with a dynamically sized PVARP then applied, where the length of that interval is extended to a predetermined percentage of the historical rate. That is, a dynamic-sized PVARP after a PVC would blank the atrial channels after an ectopic beat, thereby preventing retrograde conducted ectopic sensed beats from causing PMT, yet, at the same time, allowing sufficient atrial blanking without atrial undersensing. One method for determining the dynamic PVARP size would be some percentage (90%, for example) of the previous R-R interval. This should be sufficiently long to prevent retrograde conduction from the ectopic beat, yet short enough to prevent atrial undersensing. It can be seen, then, that the present invention offers significant utility in limiting pacemaker-mediated tachycardia. In addition, because ventricular events following an atrial event can more accurately be identified as being ectopic in origin, event markers applied to electrograms can be more accurately applied for proper classification of non-sinus sensed ventricular events vs. sinus beats, and HRV calculations that rely on sinus beats will be more accurate.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A method of improved ectopic beat detection by an implantable cardiac rhythm management device comprising the steps of:
   (a) providing a cardiac rhythm management device having an atrial event detector, a ventricular event detector and a microprocessor-based controller coupled to the atrial event detector and the ventricular event detector and programmed to determine PR intervals, RR intervals and AA intervals from detected atrial and ventricular events;
   (b) determining an average time interval between an atrial event and next occurring ventricular event over a predetermined number of heartbeat cycles ($PR_{AVG}$);
   (c) indicating an ectopic beat when a PR interval of a given heartbeat cycle is less than about 80 percent of $PR_{AVG}$ and less than about 80 ms in length; and
   (d) determining whether said given heartbeat cycle is possibly ectopic when the PR interval of said given heartbeat cycle is less than about 80 percent of $PR_{AVG}$ and the PR interval of said given heartbeat cycle is greater than about 80 ms.

2. The method of claim 1 wherein the step of determining whether said given heartbeat cycle is possibly ectopic comprises:
   (a) computing whether a ratio of a RR interval for said given heartbeat cycle to the AA interval of the said heartbeat cycle is less than about 90 percent of the RR to AA ratio for an immediately preceding heartbeat cycle;
   (b) computing whether the ratio of the length of the PR interval of said given heartbeat cycle to the length of the PR interval for an immediately preceding heartbeat cycle is less than about 60 percent;
   (c) determining that a ventricular depolarization followed the atrial depolarization in the given heartbeat cycle; and (d) determining whether a QRS complex of said given heartbeat cycle is by biphasic.

3. A method for identifying ectopic beats using an implantable cardiac rhythm management device comprising the steps of:
   (a) providing an implantable cardiac rhythm management device having a means for sensing atrial depolarization signals (P-waves), means for sensing ventricular depolarization signals (R-waves), and a microprocessor-based controller coupled to receive the P-waves and the R-waves signals;
   (b) programming the microprocessor-based controller to measure an average time interval length between the occurrence of a P-wave and a next subsequently occurring R-wave over a predetermined number of heartbeat cycles ($PR_{AVG}$);
   (c) determining whether the time interval length between a given P-wave and a next subsequently occurring R-wave (PR interval) is less than a predetermined percentage of the measured $PR_{AVG}$;
   (d) determining whether the PR interval falls into a non-physiologic range;
   (e) declaring the next subsequently occurring R-wave following the given P-wave as an ectopic beat when the determination made in steps (c) and (d) are both true;
   (f) determining whether the PR interval is physiologic when said determination made in step (c) is true and the determination made in step (d) is false; and
   (g) declaring the next subsequently occurring R-wave following said given P-wave as a normal beat when the PR interval is determined to be physiologic.

4. The method as in claim 3 wherein said predetermined percentage is less than about 80 percent.

5. The method as in claim 3 wherein said non-physiologic range is a PR interval that is less than about 80 ms.

6. The method as in claim 3 and further including the step of:
   (a) providing a dynamic PVARP for one heartbeat cycle following detection of an ectopic beat.

* * * * *